(12) United States Patent
Kashu et al.

(10) Patent No.: US 10,551,329 B2
(45) Date of Patent: Feb. 4, 2020

(54) CHECKING DEVICE

(71) Applicant: Sumitomo Chemical Company, Limited, Tokyo (JP)

(72) Inventors: Koji Kashu, Niihama (JP); Daizaburo Yashiki, Niihama (JP)

(73) Assignee: SUMITOMO CHEMICAL COMPANY, LIMTED, Tokyo (JP)

( * ) Notice: Subject to any disclaimer, the term of this patent is extended or adjusted under 35 U.S.C. 154(b) by 0 days.

(21) Appl. No.: 16/120,890

(22) Filed: Sep. 4, 2018

(65) Prior Publication Data
US 2019/0079029 A1 Mar. 14, 2019

(30) Foreign Application Priority Data

Sep. 8, 2017 (JP) .................. 2017-173486
Aug. 27, 2018 (JP) .................. 2018-158656

(51) Int. Cl.
  *G01N 23/00* (2006.01)
  *G01N 23/046* (2018.01)
  *G06T 3/40* (2006.01)

(52) U.S. Cl.
  CPC ..... *G01N 23/046* (2013.01); *G01N 2223/652* (2013.01); *G06T 3/4038* (2013.01)

(58) Field of Classification Search
  CPC .......... G10N 23/046; G01N 2223/652; G01N 23/04; G06T 3/4038; G01V 3/12
  See application file for complete search history.

(56) References Cited

U.S. PATENT DOCUMENTS

| 8,165,265 B2 * | 4/2012 | Niwa | ................... G06T 11/003 378/27 |
| 2016/0041110 A1 | 2/2016 | Matoba et al. | |

FOREIGN PATENT DOCUMENTS

| EP | 0166567 A2 | 1/1986 | |
| JP | S6122841 A | 1/1986 | |
| JP | 3717491 B2 * | 11/2005 | ............. G01N 23/04 |
| JP | 201420910 A | 2/2014 | |
| JP | 201638350 A | 3/2016 | |

* cited by examiner

*Primary Examiner* — Kiho Kim
(74) *Attorney, Agent, or Firm* — Panitch Schwarze Belisario & Nadel LLP (57) ABSTRACT

The present invention makes it possible to check a target object highly accurately and quickly. Each of the electromagnetic wave reception regions includes m pieces of smaller regions which are arranged along a diameter of a circle in a plan view of a circular profile surface.

6 Claims, 8 Drawing Sheets

CHECKING DEVICE

This Nonprovisional application claims priority under 35 U.S.C. § 119 on Patent Application No. 2017-173486 filed in Japan on Sep. 8, 2017 and Patent Application No. 2018-158656 filed in Japan on Aug. 27, 2018, the entire contents of which is hereby incorporated by reference.

TECHNICAL FIELD

The present invention relates to a checking device.

BACKGROUND ART

Nonaqueous electrolyte secondary batteries such as a lithium-ion secondary battery are in wide use as batteries for devices such as a personal computer, a mobile telephone, and a portable information terminal. Among those, attention is being given to the lithium-ion secondary battery as a battery that reduces carbon dioxide emissions and contributes to energy saving, as compared with conventional secondary batteries.

Conventionally, separator rolls in each of which a nonaqueous electrolyte secondary battery separator is wound around a core have been developed. In addition, studies are being carried out in regard to checking for detecting foreign substances adhering to the separator roll.

As an example of check for detecting foreign substances adhering to a target object, a technique is disclosed in Patent Literature 1. In the technique disclosed in Patent Literature 1, an X-ray emitted from an X-ray source is converted into parallel X-rays by a capillary lens, then a sample which is a target object is irradiated with the parallel X-rays, and then a time delay integration (TDI) sensor receives the parallel X-rays which have passed through the sample. The TDI sensor employs, for example, a technique disclosed in Patent Literature 2.

In a case of detecting foreign substances adhering to a target object having a surface whose profile is a circle (e.g., a lateral surface of a separator roll), the following checking method may be employed. Note that, hereinafter, the surface of the target object whose profile is a circle is also referred to as "circular profile surface".

That is, the target object is rotated about an axis that (i) passes through a center of a circle constituting a profile of the circular profile surface and (ii) extends in a direction substantially perpendicular to the circular profile surface. Then, the circular profile surface is irradiated with an electromagnetic wave. Then, a TDI sensor receives the electromagnetic wave which has passed through the target object. Then, images obtained when the TDI sensor has received the electromagnetic waves are analyzed, and thus a foreign substance adhering to the target object is detected. From this, the detection of foreign substances can be carried out highly efficiently, and this makes it possible to enhance a speed of the check, as compared with the technique disclosed in Patent Literature 1.

CITATION LIST

Patent Literature

Patent Literature 1: Japanese Patent Application Publication Tokukai No. 2016-38350 (Publication Date: Mar. 22, 2016)

Patent Literature 2: Japanese Patent Application Publication Tokukaisho No. 61-22841 (Publication Date: Jan. 31, 1986)

SUMMARY OF INVENTION

Technical Problem

In general, a plurality of pixels constituting the TDI sensor are arranged in a matrix manner, and images are uniformly obtained at the respective plurality of pixels. The following description will discuss, with reference to (a) through (c) of FIG. 8, a problem which occurs in this general example case, specifically, a case where an electromagnetic wave source 2000 is placed on an axis 400 which (i) passes through a center 300 of a circle constituting a profile of a circular profile surface 200b (and a circular profile surface 200a) of the above described target object 100 and (ii) extends in a direction substantially perpendicular to the circular profile surface 200b, and check is carried out while rotating the target object 100 about the axis 400. Here, pixels constituting a pixel row A, which includes a point whose distance from the center 300 in the plan view of the circular profile surface 200b can be regarded as substantially WA (hereinafter, simply referred to as "distance WA"), are indicated as pixels A1 through Ap, and obtainment target regions on the circular profile surface 200b, through which regions electromagnetic waves 2100 from the electromagnetic wave source 2000 are to be received by the respective pixels A1 through Ap, are indicated as regions EA1 through EAp. Pixels constituting a pixel row B, which includes a point whose distance from the center 300 can be regarded as substantially WB (which is different from the distance WA), are indicated as pixels B1 through Br, and obtainment target regions on the circular profile surface 200b, through which regions electromagnetic waves 2100 are to be received by the respective pixels B1 through Br, are indicated as regions EB1 through EBr. Note that, for convenience, an arbitrary one of the pixels A1 through Ap and an arbitrary one of the pixels B1 through Br are referred to as "pixel Am" and "pixel Bn", respectively. Similarly, for convenience, an arbitrary one of the regions EA1 through EAp and an arbitrary one of the regions EB1 through EBr are referred to as "region EAm" and "region EBn", respectively. Moreover, a portion of a pixel, which portion receives an electromagnetic wave 2100 from the center 300, is referred to as "point 300'".

Figure 8:
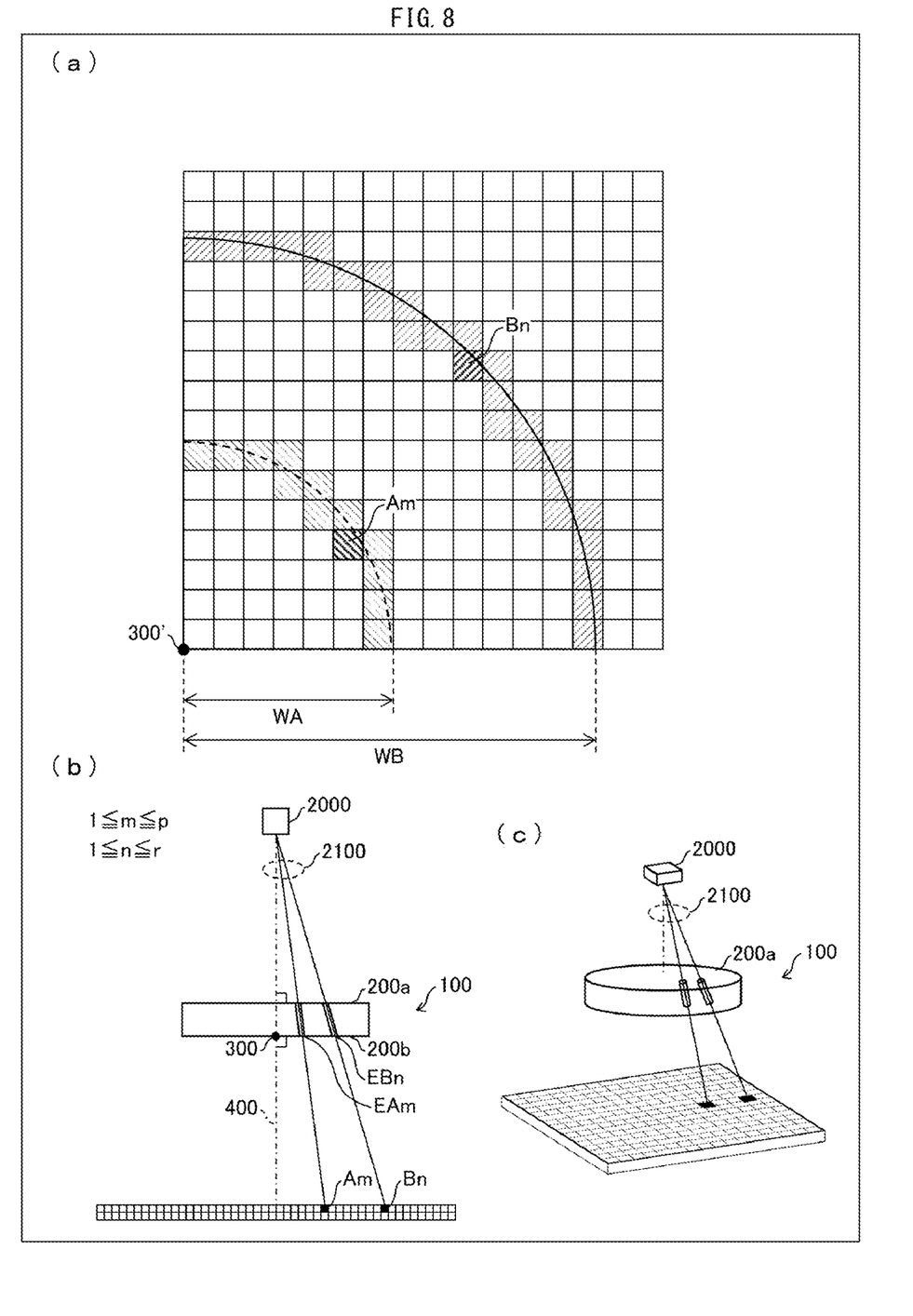
FIG. 8 is a view for explaining, in (a) through (c), a problem of a conventional technique.

In a case where the target object 100, which is moving, is irradiated with the electromagnetic wave 2100, electromagnetic waves 2100 which have passed through a particular region of the target object 100 at different points in time are received by respective different pixels. The TDI sensor obtains an analytical image by adding up pieces of information of the electromagnetic waves 2100 which passed through the same region at different points in time.

In the check, the pixels A1 through Ap receive respective electromagnetic waves 2100 which have passed through a region EAm on the target object 100 which is being rotated about the axis 400, and an analytical image piece APAm is obtained by adding up pieces of information of those electromagnetic waves 2100. This operation is carried out for all the regions EA1 through EAp, and an analytical image APA is obtained by combining analytical image pieces APA1 through APAp.

Similarly, the pixels B1 through Br receive respective electromagnetic waves 2100 which have passed through a region EBn on the target object 100 which is being rotated about the axis 400, and an analytical image piece APBn is obtained by adding up pieces of information of those electromagnetic waves 2100. Here, in the plan view of the circular profile surface 200b, distances from the center 300 to the region EAm and to the region EBn are different. Therefore, the number of pixels B1 through Br which receive respective electromagnetic waves 2100 that have passed through the region EBn is different from the number of pixels A1 through Ap which receive respective electromagnetic waves 2100 that have passed through the region EAm. As a result, in a case where pieces of information received by the respective pixels B1 through Br are to be added up based on intervals between the pixels A1 through Ap, pieces of information of electromagnetic waves 2100 which have passed through a region EBo which is different from the region EBn are added up, and therefore an obtained analytical image piece APBn becomes blurred. The converse is also true.

The inventors of the present application have found the followings: that is, in the above described check which is carried out while the target object is rotated, it is impossible to simultaneously obtain clear images of an entire region to be checked, and accordingly a problem of low accuracy in the check occurs.

An object of an aspect of the present invention is to provide a checking device which makes it possible to check a target object highly accurately and quickly.

Solution to Problem

In order to attain the object, a checking device in accordance with an aspect of the present invention is a checking device for checking a target object having a circular profile surface, which is a surface whose profile is a circle, while rotating the target object about an axis that passes through a center of the circle and extends in a direction substantially perpendicular to the circular profile surface, the checking device including: at least one electromagnetic wave source which irradiates the target object, which is being checked, with an electromagnetic wave that passes through the circular profile surface; and n pieces of electromagnetic wave reception regions for receiving the electromagnetic wave which has passed through the target object that is being checked, each of the n pieces of electromagnetic wave reception regions having m pieces of smaller regions, each of m and n being a natural number which is 2 or greater, and m×n pieces of smaller regions being arranged so as to satisfy any of (1) and (2) below:

(1) For each of the n pieces of electromagnetic wave reception regions, the m pieces of smaller regions are aligned along a diameter of the circle in a plan view of the circular profile surface.

(2) As compared with an arrangement of (1), at least one set among sets of n pieces of smaller regions, which are apart from the center of the circle by identical distances, is arranged by being rotated about the axis.

Advantageous Effects of Invention

According to an aspect of the present invention, it is possible to check a target object highly accurately and quickly.

DESCRIPTION OF EMBODIMENTS

The following description will discuss embodiments of the present invention with reference to FIGS. 1 through 7.

Figure 1:
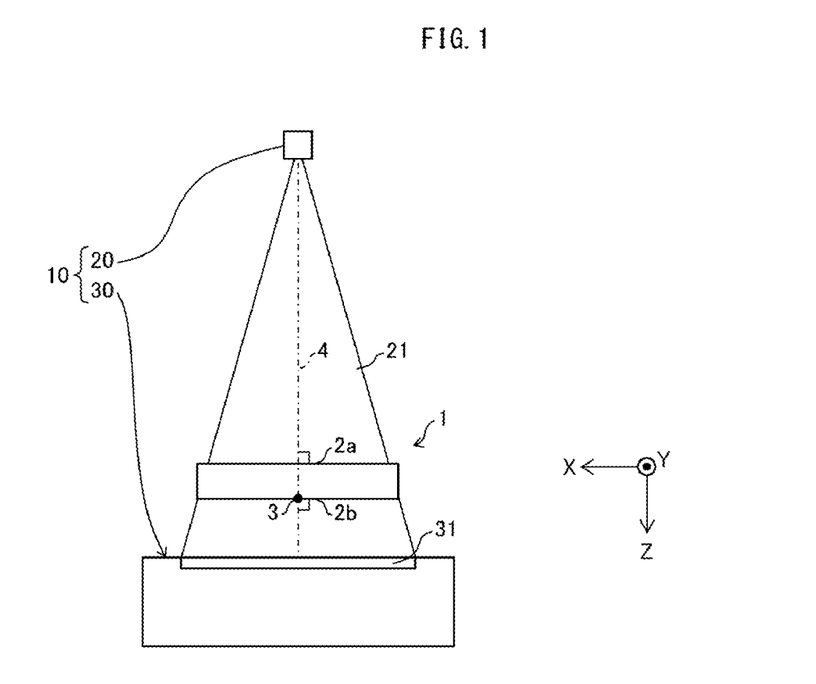
FIG. 1 is a schematic view illustrating a checking device in accordance with Embodiment 1 and Embodiment 2 of the present invention.

FIG. 1 is a schematic view illustrating a checking device 10 in accordance with Embodiment 1 and Embodiment 2 of the present invention. The checking device 10 checks a target object 1, specifically, detects a foreign substance that is adhering to the target object 1. The checking device 10 includes an electromagnetic wave source 20 and a sensor 30.

The target object 1 has a circular profile surface 2a and a circular profile surface 2b each of which is a surface whose profile is a circle. In FIG. 1, the circular profile surface 2a is located on an electromagnetic wave source 20 side, and the circular profile surface 2b is located on a sensor 30 side. A shape of the target object 1 can be a doughnut shape, a disc shape, a cylindrical shape (see (a) of FIG. 2), a columnar shape, or the like. Specific examples of the target object 1 encompass a separator roll in which a nonaqueous electrolyte secondary battery separator is wound around a core, a core around which a nonaqueous electrolyte secondary battery separator is wound, and the like.

Figure 2:
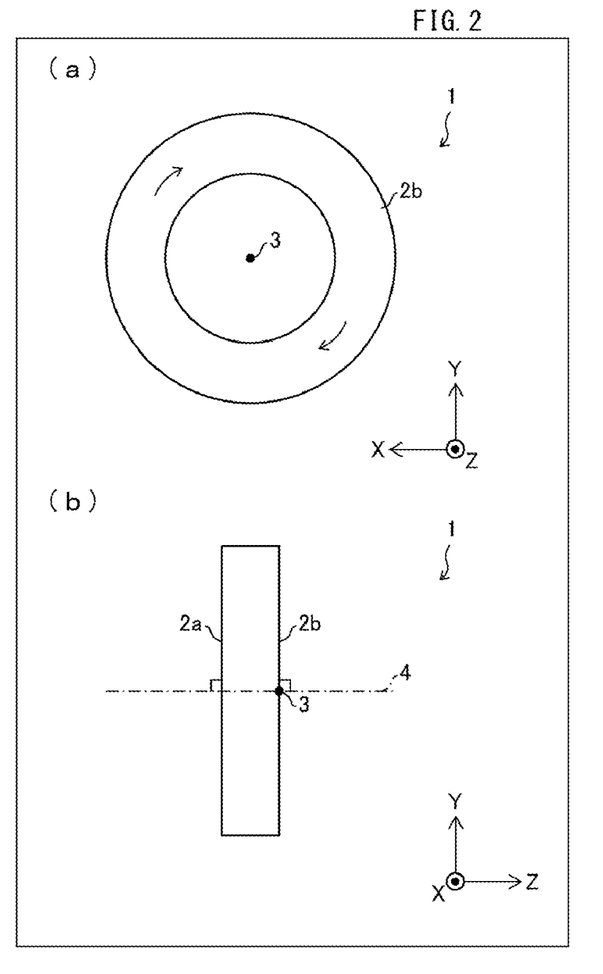
FIG. 2 is a view illustrating a state in which a target object is rotated, where (a) of FIG. 2 is a plan view of a circular profile surface, and (b) of FIG. 2 shows a lateral view of the target object.

FIG. 2 is a view illustrating a state in which the target object 1 is rotated. (a) of FIG. 2 is a plan view of the circular profile surface 2b. (b) of FIG. 2 shows a lateral view of the target object 1. Specifically, (b) of FIG. 2 illustrates a state in which the electromagnetic wave source 20 side is on the left, and the sensor 30 side is on the right.

Note that, in FIGS. 1 through 7, three directions (i.e., X direction, Y direction, and Z direction) which are perpendicular to each other are defined. The X direction is a width direction of the target object 1, the Y direction is a height direction of the target object 1, and the Z direction is a direction which is perpendicular to both the X direction and the Y direction and perpendicularly passes through the circular profile surface 2a and the circular profile surface 2b.

In a state in which the target object 1 is checked by the checking device 10, the target object 1 is rotated about an axis 4 that (i) passes through a center 3 of a circle constituting a profile of the circular profile surface 2b and (ii) extends in a direction (in parallel with the Z direction) substantially perpendicular to the circular profile surface 2b. A similar relation holds true also between the target object 1 and the circular profile surface 2a. A rotation direction is a clockwise direction in the plan view of the circular profile surface 2b. However, the rotation direction can be an anti-clockwise direction in the plan view of the circular profile surface 2b.

The electromagnetic wave source 20 irradiates the target object 1 with an electromagnetic wave 21 which passes through the circular profile surface 2a and the circular profile surface 2b. The electromagnetic wave source 20 is provided such that a direction between the electromagnetic wave source 20 and the center 3 is substantially perpendicular to the circular profile surface 2b. The electromagnetic wave 21 can be, for example, an X-ray. The electromagnetic wave 21 is emitted toward the circular profile surface 2a, then passes through the target object 1, and then exits through the circular profile surface 2b.

The sensor 30 includes an electromagnetic wave receiving section 31. The sensor 30 receives the electromagnetic wave 21, which has passed through the target object 1, on the electromagnetic wave receiving section 31, and thus obtains an image of a portion in the circular profile surface 2a and in the circular profile surface 2b through which portion the electromagnetic wave has passed. A specific configuration of the electromagnetic wave receiving section 31 will be described later, and it is possible to provide at least one lens which covers the electromagnetic wave receiving section 31.

In Embodiment 1 and Embodiment 2 below, an electromagnetic wave receiving section 31a and an electromagnetic wave receiving section 31b will respectively be described each of which is a specific configuration example of the electromagnetic wave receiving section 31.

Embodiment 1

Figure 3:
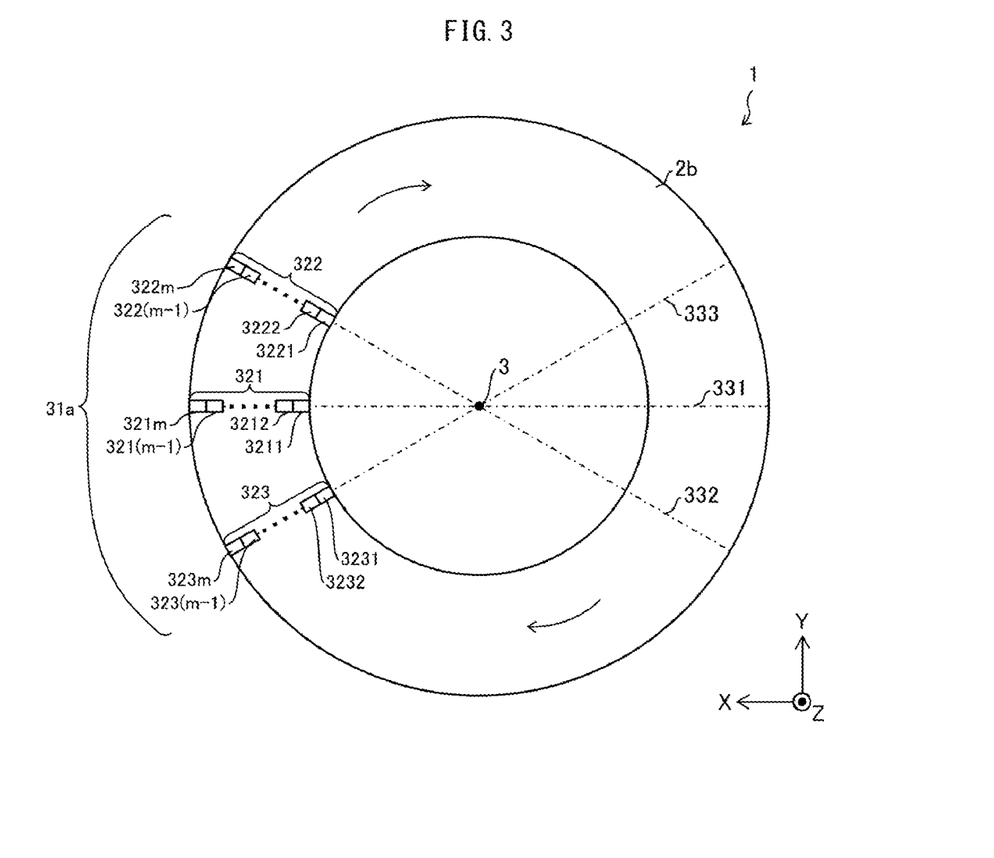
FIG. 3 is a plan view of the circular profile surface and illustrates a configuration of n pieces of electromagnetic wave reception regions in accordance with Embodiment 1 of the present invention.

FIG. 3 is a plan view of the circular profile surface 2b and illustrates a configuration of the electromagnetic wave receiving section 31a (i.e., n pieces of electromagnetic wave reception regions) in accordance with Embodiment 1 of the present invention. The electromagnetic wave receiving section 31a have three electromagnetic wave reception regions, i.e., electromagnetic wave reception regions 321 through 323.

The electromagnetic wave reception region 321 includes m pieces of smaller regions, i.e., a smaller region 3211, a smaller region 3212, ... , a smaller region 321(m−1), and a smaller region 321m. In the plan view of the circular profile surface 2b, the smaller region 3211, the smaller region 3212, ... , the smaller region 321(m−1), and the smaller region 321m are arranged, along a diameter 331 of a circle that constitutes a profile of the circular profile surface 2b, in this order from a center 3 side to a circumference side of the circle.

The electromagnetic wave reception region 322 includes m pieces of smaller regions, i.e., a smaller region 3221, a smaller region 3222, ... , a smaller region 322(m−1), and a smaller region 322m. In the plan view of the circular profile surface 2b, the smaller region 3221, the smaller region 3222, ... , the smaller region 322(m−1), and the smaller region 322m are arranged, along a diameter 332 of the circle that constitutes the profile of the circular profile surface 2b, in this order from the center 3 side to the circumference side of the circle.

The electromagnetic wave reception region 323 includes m pieces of smaller regions, i.e., a smaller region 3231, a smaller region 3232, ... , a smaller region 323(m−1), and a smaller region 323m. In the plan view of the circular profile surface 2b, the smaller region 3231, the smaller region 3232, ... , the smaller region 323(m−1), and the smaller region 323m are arranged, along a diameter 333 of the circle that constitutes the profile of the circular profile surface 2b, in this order from the center 3 side to the circumference side of the circle.

That is, in the plan view of the circular profile surface 2b, each of the electromagnetic wave reception regions 321 through 323 includes m pieces of smaller regions which are arranged along the diameter (i.e., the diameter 331, 332, or 333) of the circle that constitutes the profile of the circular profile surface 2b. Each of the smaller regions functionally corresponds to one of units which are obtained by dividing the electromagnetic wave receiving section 31a into 3×m (i.e., n×m) pieces, and includes at least one pixel.

According to the electromagnetic wave receiving section 31a, the m pieces of smaller regions of each of the electromagnetic wave reception regions 321 through 323 are arranged so as to offset increase of the rotation speed of the circular profile surface 2b (and further, of the target object 1), which speed becomes higher as a distance from the center 3 increases. According to the arrangement, it is possible to prevent a case where the number of the smaller regions (specific example: pixels) for receiving electromagnetic waves 21 which have passed through the region EBn is different from the number of the smaller regions for receiving electromagnetic waves 21 which have passed through the region EAm. Consequently, it is possible to simultaneously obtain clear images in the entire region to be checked. Therefore, it is possible to highly accurately carry out the check (quickly) in which the target object 1 is being rotated.

The electromagnetic wave reception region 321 is preferably configured, in the plan view of the circular profile surface 2b, such that suitability of smaller regions for capturing an image of a subject which moves fast is heightened as a distance from the center 3 increases (that is, the suitability becomes higher in a direction from the smaller region 3211 to the smaller region 321m). An example of a method for achieving the configuration is a method in which a shutter speed, for corresponding at least one pixel to appropriately receive an electromagnetic wave 21, is gradually heightened in a direction from the smaller region 3211 to the smaller region 321m. According to the configuration, it is possible to reduce a possibility that a blur occurs, due to the high rotation speed, in an image obtained based on an electromagnetic wave 21 received by a smaller region distant from the center 3 in the plan view of the circular profile surface 2b. The same applies to the electromagnetic wave reception region 322 and to the electromagnetic wave reception region 323, and the above described configuration can be provided in at least one of the electromagnetic wave reception regions 321 through 323.

Embodiment 2

Figure 4:
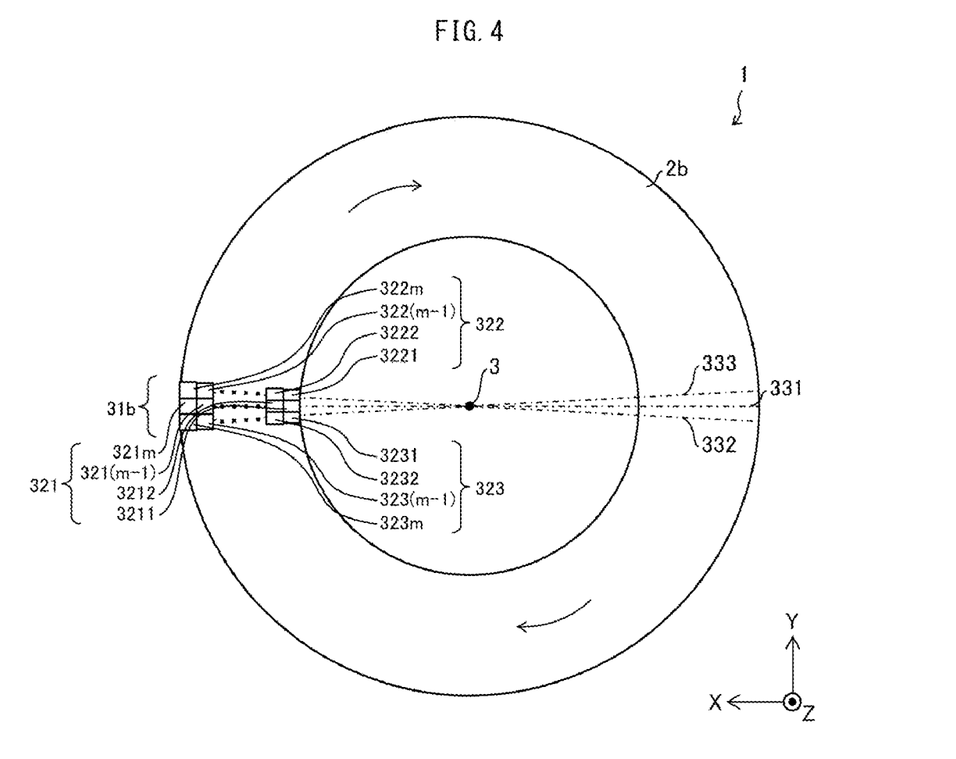
FIG. 4 is a plan view of the circular profile surface and illustrates a configuration of n pieces of electromagnetic wave reception regions in accordance with Embodiment 2 of the present invention.

FIG. 4 is a plan view of the circular profile surface 2b and illustrates a configuration of the electromagnetic wave receiving section 31b (i.e., n pieces of electromagnetic wave reception regions) in accordance with Embodiment 2 of the present invention.

The electromagnetic wave receiving section 31b has a configuration similar to that of the electromagnetic wave receiving section 31a, except for points described below. Note that, hereinafter, a "circumferential direction" means a direction along a circumference of the circle constituting the profile of the circular profile surface 2b (and the circular profile surface 2a).

In the electromagnetic wave reception region 321, a size of the smaller region 3212 in the circumferential direction is larger than that of the smaller region 3211, . . . and a size of the smaller region 321m in the circumferential direction is larger than that of the smaller region 321(m−1).

In the electromagnetic wave reception region 322, a size of the smaller region 3222 in the circumferential direction is larger than that of the smaller region 3221, . . . and a size of the smaller region 322m in the circumferential direction is larger than that of the smaller region 322(m−1).

In the electromagnetic wave reception region 323, a size of the smaller region 3232 in the circumferential direction is larger than that of the smaller region 3231, . . . and a size of the smaller region 323m in the circumferential direction is larger than that of the smaller region 323(m−1).

That is, in each of the electromagnetic wave reception regions 321 through 323, sizes of the m pieces of smaller regions in the circumferential direction become larger as a distance from the center 3 increases in the plan view of the circular profile surface 2b. According to the configuration, it is possible to increase an amount of electromagnetic wave 21 to be received by a smaller region which is distant from the center 3 in the plan view of the circular profile surface 2b, and this makes it possible to reduce a possibility that an image becomes darker which is obtained based on an electromagnetic wave 21 received by such a smaller region distant from the center 3. The above described configuration can be provided in at least one of the electromagnetic wave reception regions 321 through 323.

Moreover, in accordance with the above described configuration, the electromagnetic wave receiving section 31b schematically has a shape obtained by subtracting a sector whose arc is an inner (center 3 side) edge of the circular profile surface 2b from another sector whose arc is an outer (circumference side of circle) edge of the circular profile surface 2b.

Additional Remarks

In the above Embodiment 1 and Embodiment 2, the examples are described in which the number of electromagnetic wave reception regions is three (i.e., n=3). Note that the number of electromagnetic wave reception regions is not limited to a particular one, provided that the number is 2 or greater. In other words, n which represents the number of electromagnetic wave reception regions only needs to be a natural number which is 2 or greater.

In the above Embodiment 1 and Embodiment 2, the examples are described in which the number of smaller regions in each of the electromagnetic wave reception regions is at least four (i.e., 4 m). Note that the number of smaller regions in each of the electromagnetic wave reception regions is not limited to a particular one, provided that the number is 2 or greater. In other words, m which represents the number of smaller regions in each of the electromagnetic wave reception regions only needs to be a natural number which is 2 or greater.

The checking device 10 preferably has the following configuration. That is, the electromagnetic wave reception regions 321 through 323 receive the electromagnetic wave 21 from a certain portion of the circular profile surface 2b at respectively different points in time. Then, the checking device 10 detects a foreign substance adhering to the certain portion by analyzing an analytical image obtained by adding up three (i.e., n pieces of) images of the certain portion which have been obtained when the electromagnetic wave reception regions 321 through 323 receive the electromagnetic wave 21. The sensor 30 of the checking device 10 can be, for example, a TDI sensor.

Figure 5:
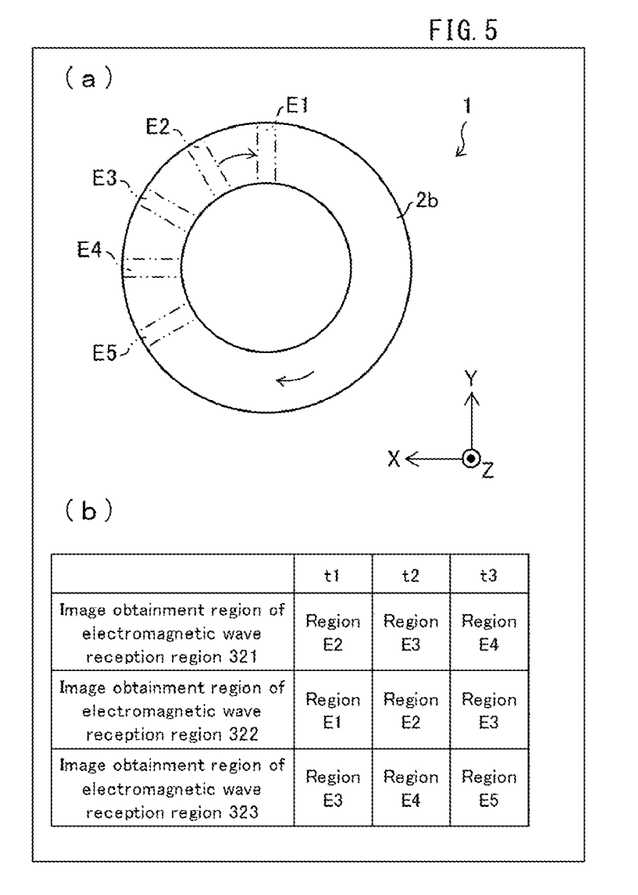
FIG. 5 illustrates a specific example of check carried out with use of the n pieces of electromagnetic wave reception regions in accordance with Embodiment 1 of the present invention, where (a) of FIG. 5 illustrates image obtainment target regions on the circular profile surface, and (b) of FIG. 5 illustrates correspondence between image obtainment target regions and electromagnetic wave reception regions for each elapsed time.

FIG. 5 illustrates a specific example of check carried out with use of the electromagnetic wave receiving section 31a. (a) of FIG. 5 illustrates regions E1 through E5 which are respective image obtainment target regions in the circular profile surface 2b. (b) of FIG. 5 illustrates correspondence between the regions E1 through E5 and the electromagnetic wave reception regions 321 through 323 for each elapsed time.

At a time t1, the electromagnetic wave reception region 321 obtains an image of the region E2, the electromagnetic wave reception region 322 obtains an image of the region E1, and the electromagnetic wave reception region 323 obtains an image of the region E3.

At a time t2 which is later than the time t1, in accordance with rotation of the target object 1, the electromagnetic wave reception region 321 obtains an image of the region E3, the electromagnetic wave reception region 322 obtains an image of the region E2, and the electromagnetic wave reception region 323 obtains an image of the region E4.

At a time t3 which is later than the time t2, in accordance with rotation of the target object 1, the electromagnetic wave reception region 321 obtains an image of the region E4, the electromagnetic wave reception region 322 obtains an image of the region E3, and the electromagnetic wave reception region 323 obtains an image of the region E5.

From this, images of the region E3 are obtained by the respective electromagnetic wave reception regions 321 through 323. Then, the checking device 10 adds up the images of the region E3 which have been obtained by the respective electromagnetic wave reception regions 321 through 323, and thus prepares an image of the region E3 for analysis. As such the checking device 10 obtains the image of the region E3 for analysis which is clearer than an image of the region E3 obtained by only one of the electromagnetic wave reception regions 321 through 323.

According to the configuration, the plurality of images of the region E3 are added up, and this makes it possible to improve accuracy in checking the region E3. The same applies to the region E1, the region E2, the region E4, and the region E5.

In FIG. 5, the regions E1 through E5 are indicated as regions of which the electromagnetic wave reception regions 321 through 323 obtain images (in other words, indicated as check target regions). Note, however, that it is possible to obtain an image of the entire circular profile surface 2b or of an arbitrary part of the circular profile surface 2b (as the check target region).

The checking device 10 can include m×n pieces of electromagnetic wave sources instead of the electromagnetic wave source 20, and each of the m×n pieces of electromagnetic wave sources can be provided such that a direction from each of the m×n pieces of electromagnetic wave sources to a corresponding one of the m pieces of smaller regions in each of n pieces of electromagnetic wave reception regions is substantially perpendicular to the circular profile surface 2b. That is, the m×n pieces of electromagnetic wave sources can be provided so as to have a one-to-one correspondence with all the respective smaller regions. The checking device 10 can include, instead of the electromagnetic wave source 20, electromagnetic wave sources whose number of pieces is less than m×n pieces and a mechanism (not illustrated) for guiding electromagnetic waves, which have been generated by the respective electromagnetic wave sources, in a direction substantially perpendicular to the smaller regions 3211 through 323m by reflection or refraction.

In a case where a direction in which an electromagnetic wave 21 enters a certain smaller region is inclined with respect to the direction substantially perpendicular to the circular profile surface 2b, misalignment may occur between the certain smaller region and the electromagnetic wave 21, depending on a thickness of the target object 1. Further, the misalignment between the certain smaller region and the electromagnetic wave 21 may become a cause of misalignment between the regions EB1 through EBr. According to the configuration, it is possible to inhibit misalignment between the certain smaller region and the electromagnetic wave 21, and it is therefore possible to reduce a possibility of misalignment that may occur between the regions EB1 through EBr.

Modification Example

Figure 6:
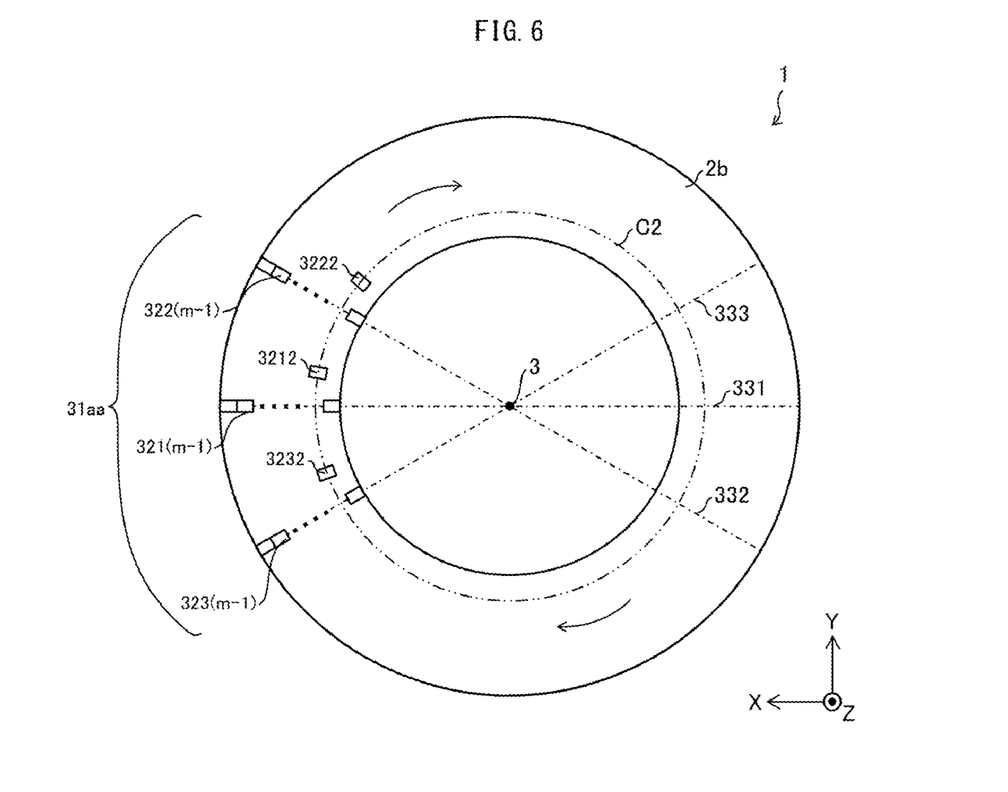
FIG. 6 is a plan view of the circular profile surface and illustrates a configuration of n pieces of electromagnetic wave reception regions in accordance with Modification Example 1 of the present invention.

FIG. 6 is a plan view of the circular profile surface 2b and illustrates a configuration of an electromagnetic wave receiving section 31aa in accordance with Modification Example 1 of the electromagnetic wave reception region 31a.

The electromagnetic wave receiving section 31aa is different from the electromagnetic wave receiving section 31a in the following point. That is, in the electromagnetic wave receiving section 31aa, the smaller region 3212, the smaller region 3222, and the smaller region 3232 are shifted along a circumference C2 whose center is the center 3, in other words, those regions are rotated about the axis 4 (see FIG. 1), as compared with the arrangement in the electromagnetic wave receiving section 31a. An angle of the rotation is not limited to a particular one.

Figure 7:
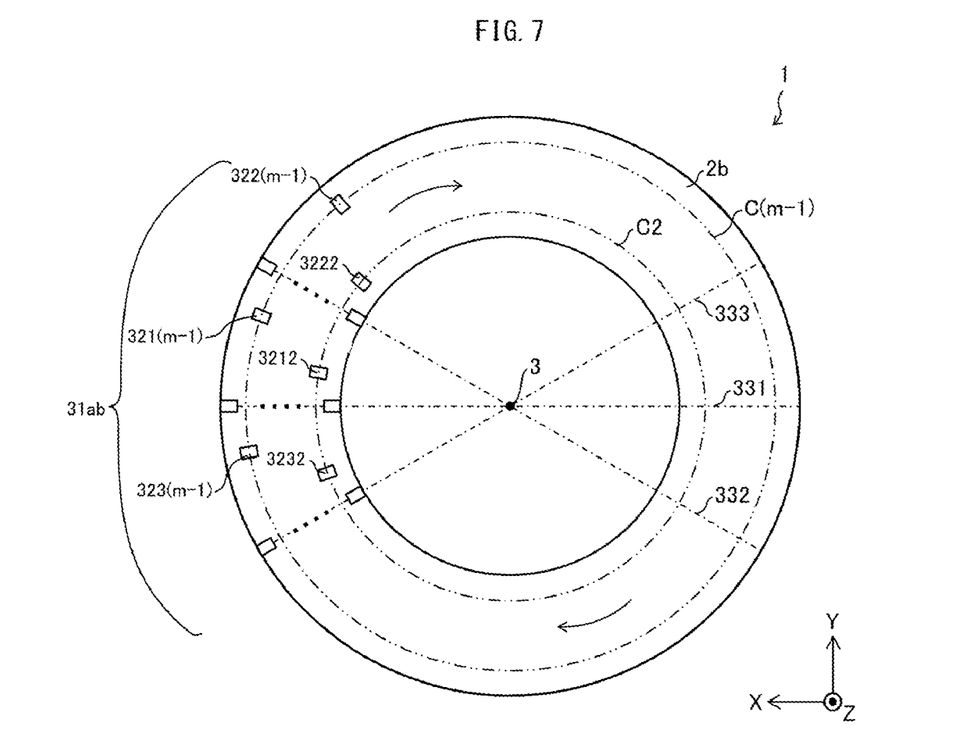
FIG. 7 is a plan view of the circular profile surface and illustrates a configuration of n pieces of electromagnetic wave reception regions in accordance with Modification Example 2 of the present invention.

FIG. 7 is a plan view of the circular profile surface 2b and illustrates a configuration of an electromagnetic wave receiving section 31ab in accordance with Modification Example 2 of the electromagnetic wave reception region 31a.

The electromagnetic wave receiving section 3 lab is different from the electromagnetic wave receiving section 31a in the following point. That is, in the electromagnetic wave receiving section 31ab, the smaller region 3212, the smaller region 3222, and the smaller region 3232 are shifted along a circumference C2 whose center is the center 3, in other words, those regions are rotated about the axis 4, as compared with the arrangement in the electromagnetic wave receiving section 31a. Further, in the electromagnetic wave receiving section 3 lab, the smaller region 321(m−1), the smaller region 322(m−1), and the smaller region 323(m−1) are shifted along a circumference C(m−1) whose center is the center 3, in other words, those regions are rotated about the axis 4, as compared with the arrangement in the electromagnetic wave receiving section 31a. In the electromagnetic wave receiving section 31ab, angles of those rotations are different from each other. Note, however, that the angles of those rotations can be identical with each other.

In each of the electromagnetic wave receiving section 31aa and the electromagnetic wave receiving section 3 lab, at least one set among sets of three smaller regions, which are apart from the center 3 by the same distance, is rotated about the axis 4, as compared with the arrangement in the electromagnetic wave receiving section 31a. In the electromagnetic wave receiving section 31a, the "sets of three smaller regions" are m sets of smaller regions, i.e., a set of the smaller region 3211, the smaller region 3221, and the smaller region 3231, a set of the smaller region 3212, the smaller region 3222, and the smaller region 3232, . . . , a set of the smaller region 321(m−1), the smaller region 322(m−1), and the smaller region 323(m−1), and a set of the smaller region 321m, the smaller region 322m, and the smaller region 323m.

[Recap]

The checking device in accordance with an aspect of the present invention is a checking device for checking a target object having a circular profile surface, which is a surface whose profile is a circle, while rotating the target object about an axis that passes through a center of the circle and extends in a direction substantially perpendicular to the circular profile surface, the checking device including: at least one electromagnetic wave source which irradiates the target object, which is being checked, with an electromagnetic wave that passes through the circular profile surface; and n pieces of electromagnetic wave reception regions for receiving the electromagnetic wave which has passed through the target object that is being checked, each of the n pieces of electromagnetic wave reception regions having m pieces of smaller regions, each of m and n being a natural number which is 2 or greater, and m×n pieces of smaller regions being arranged so as to satisfy any of (1) and (2) below:

(1) For each of the n pieces of electromagnetic wave reception regions, the m pieces of smaller regions are aligned along a diameter of the circle in a plan view of the circular profile surface.

(2) As compared with an arrangement of (1), at least one set among sets of n pieces of smaller regions, which are apart from the center of the circle by identical distances, is arranged by being rotated about the axis.

According to the configuration, the m pieces of smaller regions of each of the n pieces of electromagnetic wave reception regions are arranged so as to offset increase of the rotation speed of the circular profile surface (and further, of the target object), which speed becomes higher as a distance from the center of the circular profile surface increases. According to the arrangement, it is possible to prevent a case where the number of pixels for receiving electromagnetic waves which have passed through the region EBn is different from the number of pixels for receiving electromagnetic waves which have passed through the region EAm. Consequently, it is possible to simultaneously obtain clear images in the entire region to be checked. Therefore, it is possible to highly accurately carry out the check (quickly) in which the target object is being rotated.

In the checking device in accordance with an aspect of the present invention, it is preferable that, in at least one of the n pieces of electromagnetic wave reception regions, the m pieces of smaller regions have respective sizes that become larger in a direction along a circumference of the circle as a distance from the center of the circle increases in the plan view of the circular profile surface.

According to the configuration, it is possible to increase an amount of electromagnetic wave to be received by a smaller region distant from the center of the circle in the plan view of the circular profile surface, and this makes it possible to reduce a possibility that an image becomes darker which is obtained based on an electromagnetic wave received by such a smaller region distant from the center.

In the checking device in accordance with an aspect of the present invention, it is preferable that, in at least one of the n pieces of electromagnetic wave reception regions, suitability of the m pieces of smaller regions for capturing an image of a subject which moves fast is heightened as a distance from the center of the circle increases in the plan view of the circular profile surface.

According to the configuration, it is possible to reduce a possibility that a blur occurs, due to the high rotation speed, in an image obtained based on an electromagnetic wave received by a smaller region distant from the center of the circle in the plan view of the circular profile surface.

In the checking device in accordance with an aspect of the present invention, it is preferable that the at least one electromagnetic wave source is m×n pieces of electromagnetic wave sources, each of the m×n pieces of electromagnetic wave sources being provided such that a direction from each of the m×n pieces of electromagnetic wave sources to a corresponding one of the m pieces of smaller regions in each of the n pieces of electromagnetic wave reception regions is substantially perpendicular to the circular profile surface.

In a case where a direction in which an electromagnetic wave enters a certain smaller region is inclined with respect to the direction substantially perpendicular to the circular profile surface, misalignment may occur between the certain smaller region and the electromagnetic wave, depending on a dimension of the target object (hereinafter, also referred to as "thickness of target object") in the direction substantially perpendicular to the circular profile surface. Further, the misalignment between the certain smaller region and the electromagnetic wave may become a cause of misalignment between the regions EB1 through EBr. According to the configuration, it is possible to inhibit misalignment between the certain smaller region and the electromagnetic wave, and it is therefore possible to reduce a possibility of misalignment that may occur between the regions EB1 through EBr.

In the checking device in accordance with an aspect of the present invention, it is preferable that the at least one electromagnetic wave source is one electromagnetic wave source, the one electromagnetic wave source being provided such that a direction from the one electromagnetic wave source to the center of the circle becomes substantially perpendicular to the circular profile surface.

According to the configuration, it is possible to uniformly irradiate the smaller regions with electromagnetic waves, and this makes it possible to reduce a possibility that an image obtained from an electromagnetic wave received by a particular smaller region becomes darker.

In the checking device in accordance with an aspect of the present invention, it is preferable that the n pieces of electromagnetic wave reception regions receive the electromagnetic wave from a certain portion of the circular profile surface at respectively different points in time; and the checking device detects a foreign substance adhering to the certain portion by analyzing an analytical image which has been obtained by adding up n pieces of images of the certain portion, the n pieces of images being obtained when the n pieces of electromagnetic wave reception regions receive the electromagnetic wave.

According to the configuration, it is possible to improve accuracy of the check by adding up a plurality of images of the same portion in a manner of the TDI sensor.

The present invention is not limited to the embodiments, but can be altered by a skilled person in the art within the scope of the claims. The present invention also encompasses, in its technical scope, any embodiment derived by combining technical means disclosed in differing embodiments.

REFERENCE SIGNS LIST

1: Target object
2a and 2b: Circular profile surface
3: Center
4: Axis
10: Checking device
20: Electromagnetic wave source
21: Electromagnetic wave
30: Sensor
31, 31a, 31aa, 31ab, and 31b: Electromagnetic wave receiving section
321 through 323: Electromagnetic wave reception region
3211 through 323m: Smaller region
331 through 333: Diameter

The invention claimed is:

1. A checking device for checking a target object having a circular profile surface, which is a surface whose profile is a circle, while rotating the target object about an axis that passes through a center of the circle and extends in a direction substantially perpendicular to the circular profile surface, said checking device comprising:
at least one electromagnetic wave source which irradiates the target object, which is being checked, with an electromagnetic wave that passes through the circular profile surface; and
n pieces of electromagnetic wave reception regions for receiving the electromagnetic wave which has passed through the target object that is being checked, each of the n pieces of electromagnetic wave reception regions having m pieces of smaller regions, each of m and n being a natural number which is 2 or greater, and
m×n pieces of smaller regions being arranged so as to satisfy any of (1) and (2) below:
(1) for each of the n pieces of electromagnetic wave reception regions, the m pieces of smaller regions are aligned along a diameter of the circle in a plan view of the circular profile surface and;
(2) as compared with an arrangement of (1), at least one set among sets of n pieces of smaller regions, which are apart from the center of the circle by identical distances, is arranged by being rotated about the axis.

2. The checking device as set forth in claim 1, wherein:
in at least one of the n pieces of electromagnetic wave reception regions, the m pieces of smaller regions have respective sizes that become larger in a direction along a circumference of the circle as a distance from the center of the circle increases in the plan view of the circular profile surface.

3. The checking device as set forth in claim 1, wherein:
in at least one of the n pieces of electromagnetic wave reception regions, suitability of the m pieces of smaller regions for capturing an image of a subject which moves fast is heightened as a distance from the center of the circle increases in the plan view of the circular profile surface.

4. The checking device as set forth in claim 1, wherein:
the at least one electromagnetic wave source is m×n pieces of electromagnetic wave sources, each of the m×n pieces of electromagnetic wave sources being provided such that a direction from each of the m×n pieces of electromagnetic wave sources to a corresponding one of the m pieces of smaller regions in each of the n pieces of electromagnetic wave reception regions is substantially perpendicular to the circular profile surface.

5. The checking device as set forth in claim 1, wherein:
the at least one electromagnetic wave source is one electromagnetic wave source, the one electromagnetic wave source being provided such that a direction from the one electromagnetic wave source to the center of the circle becomes substantially perpendicular to the circular profile surface.

6. The checking device as set forth in claim 1, wherein:
the n pieces of electromagnetic wave reception regions receive the electromagnetic wave from a certain portion of the circular profile surface at respectively different points in time; and
said checking device detects a foreign substance adhering to the certain portion by analyzing an analytical image which has been obtained by adding up n pieces of images of the certain portion, the n pieces of images being obtained when the n pieces of electromagnetic wave reception regions receive the electromagnetic wave.

* * * * *